US00PP27725P2

(12) United States Plant Patent
Johnson, Jr.

(10) Patent No.: US PP27,725 P2
(45) Date of Patent: Feb. 28, 2017

(54) ***BEGONIA* PLANT NAMED 'PLUM PAISLEY'**

(50) Latin Name: ***Begonia* hybrid**
Varietal Denomination: Plum Paisley

(71) Applicant: Ozzie W. Johnson, Jr., Marietta, GA (US)

(72) Inventor: Ozzie W. Johnson, Jr., Marietta, GA (US)

(73) Assignee: ITS ALL PLANTS LLC, Alpharetta, GA (US)

( * ) Notice: Subject to any disclaimer, the term of this patent is extended or adjusted under 35 U.S.C. 154(b) by 0 days.

(21) Appl. No.: 13/998,167

(22) Filed: Oct. 8, 2013

(51) Int. Cl.
*A01H 5/02* (2006.01)

(52) U.S. Cl.
USPC ..... Plt./343

(58) Field of Classification Search
USPC ..... Plt./343
See application file for complete search history.

(56) References Cited

PUBLICATIONS

Jensen Nursery, Feb. 11, 2013.*

* cited by examiner

*Primary Examiner* — Keith Robinson
(74) *Attorney, Agent, or Firm* — Penny J. Aguirre

(57) ABSTRACT

A new cultivar of *Begonia* of hybrid origin named 'Plum Paisley', that is characterized by its large leaves reaching up to 25 cm in length, its large plant size reaching 30 cm in height and up to 46 cm in spread, its plant habit typical of Rex *Begonias*, its foliage with that emerges light green with dark green on the margins and surrounding the central vein, then develops silver mottling of polka dots near the margin that coalesce into a central area of silver mottling that develops a purple sheen when mature, and its pink flowers that rise about 5 cm above the foliage.

2 Drawing Sheets

Botanical classification: *Begonia* hybrid.
Cultivar designation: 'Plum Paisley'.

BACKGROUND OF THE INVENTION

The present invention relates to a new and distinct cultivar of *Begonia* plant of hybrid origin, botanically known as *Begonia* 'Plum Paisley' and will be referred to hereafter by its cultivar name, 'Plum Paisley'.

'Plum Paisley' originated as a seedling that arose from seed planted from open pollination of 'Georgia Tasker' (not patented) in Marietta, Ga. 'Plum Paisley' was selected as a single unique plant in April of 2011 from amongst the resulting seedlings. The male parent is unknown.

Asexual propagation of the new cultivar was first accomplished by stem and leaf cuttings in Alpharetta, Ga. in August of 2011 by the Inventor. Asexual propagation by stem cuttings, leaf cuttings, and in vitro propagation has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Plum Paisley' as a new and distinct cultivar of *Begonia*.

1. 'Plum Paisley' exhibits large leaves reaching up to 25 cm in length.
2. 'Plum Paisley' exhibits a large plant size reaching about 30 cm in height and up to 46 cm in spread.

3. 'Plum Paisley' exhibits a plant habit typical of Rex *Begonias* (*Begonia* Rex-cultorum group).
4. 'Plum Paisley' exhibits foliage that emerges light green with dark green on the margins and surrounding the central vein, then develops silver mottling of polka dots near the margin that coalesce into a central area of silver mottling that develops a purple sheen when mature.
5. 'Plum Paisley' exhibits pink flowers that rise about 5 cm above the foliage.

The female parent of 'Plum Paisley', 'Georgia Tasker', differs from 'Plum Paisley' in having foliage that is bright to deep green with a burgundy margin and a wide burgundy center. 'Plum Paisley' can be most closely compared to the cultivars 'Annie' (not patented) and 'Maui Mist' (U.S. Plant Pat. No. 11,934). 'Annie' is similar to 'Plum Paisley' in leaf pattern but differs from 'Plum Paisley' in having smaller leaves that become more red in tone rather than purple with the lower surface red in color, in having leaves that are softer in texture with two large serrations on the larger side of the asymmetrical side of the leaf, and in lacking blooms when grown under the same conditions as 'Plum Paisley'. 'Maui Mist' differs from 'Plum Paisley' in having leaves that are more round in shape with a texture that is softer and less puckered and become pinkish-red on the upper surface and red on the lower surface, and in having petioles with greater pubescence.

BRIEF DESCRIPTION OF THE DRAWINGS

The accompanying colored photographs illustrate the overall appearance and distinct characteristics of the new

*Begonia*. The photographs were taken of plants approximately 3 months in age as grown in a one-gallon container under greenhouse conditions with light shade in Alpharetta, Ga.

Figure 1:
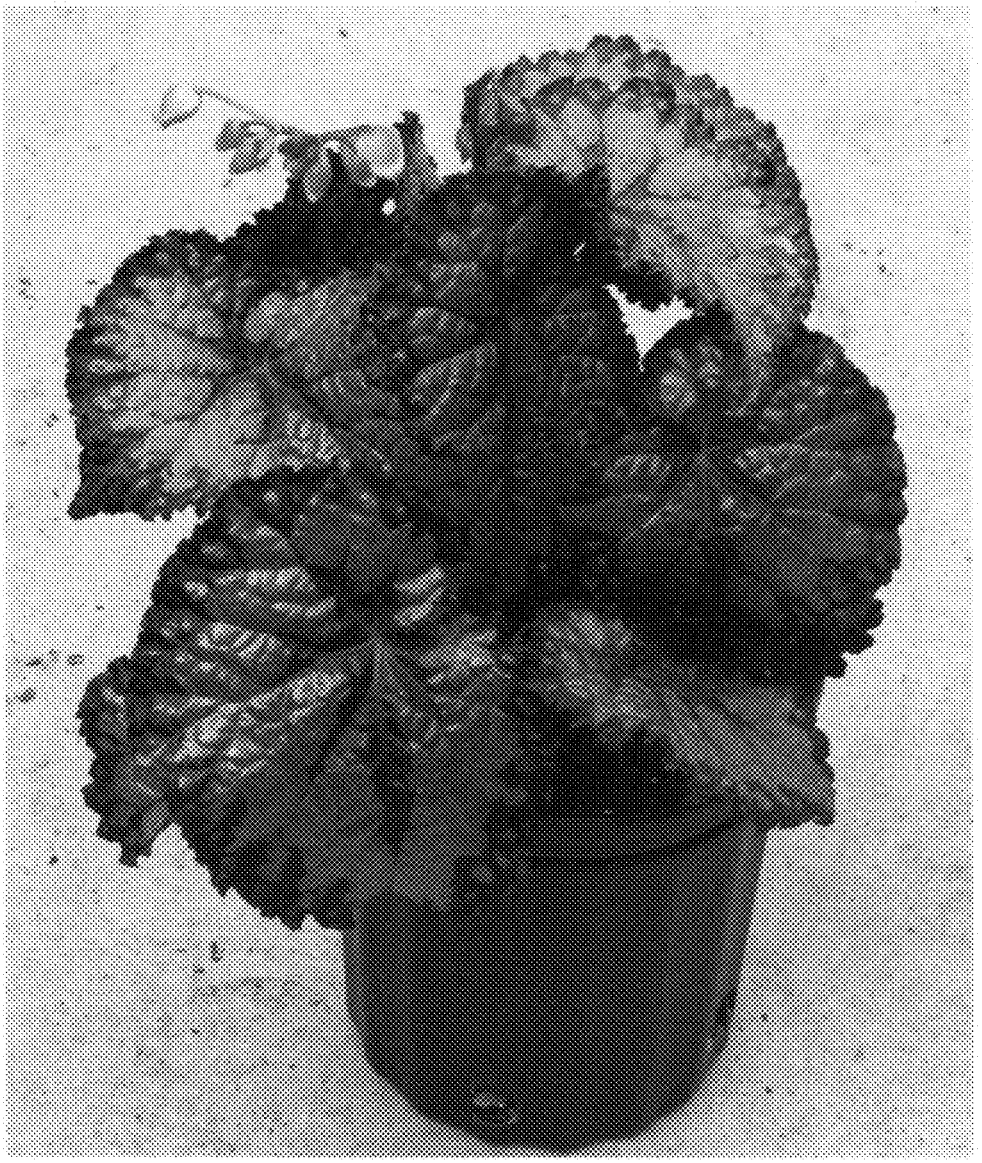

The photograph in FIG. 1 provides a side view of 'Plum Paisley' in bloom.

Figure 2:
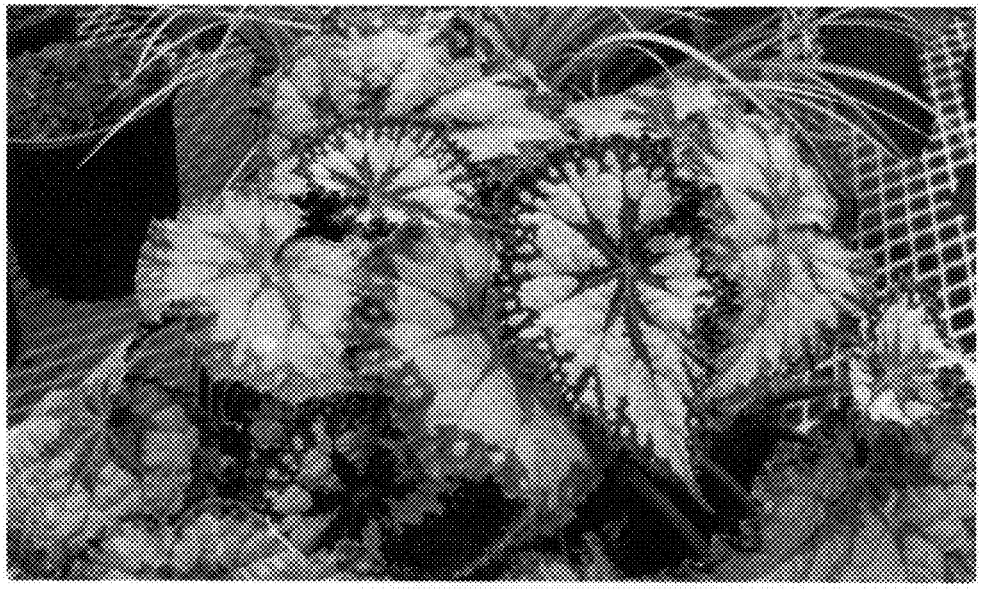

The photograph in FIG. 2 provides a view of the young and mature foliage of 'Plum Paisley'.

Figure 3:
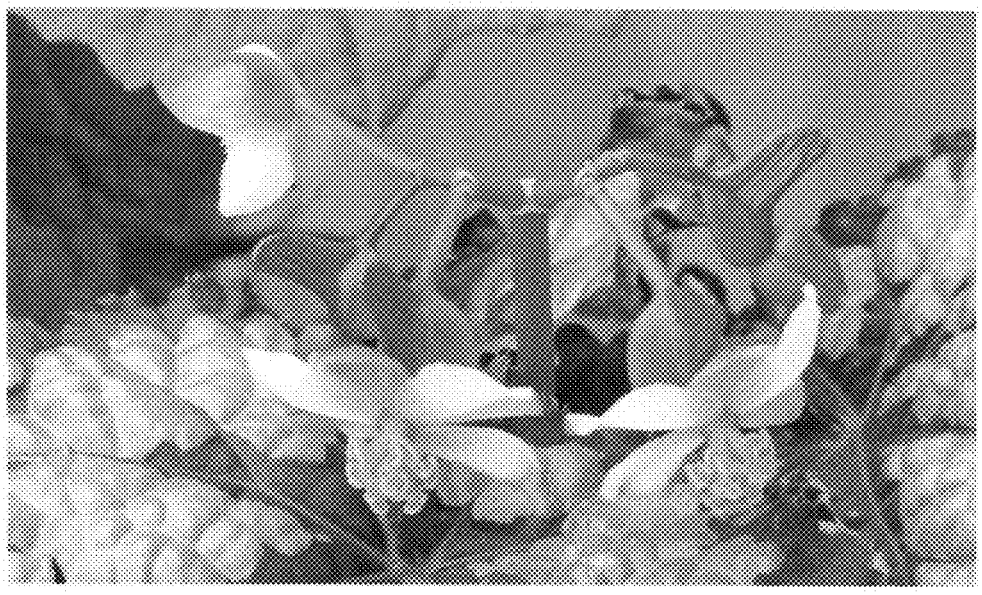

The photograph in FIG. 3 provides a view of the flowers of 'Plum Paisley'.

The colors in the photographs may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 3 months in age as grown in one-gallon containers under greenhouse conditions with light shade in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous tuberous perennial in tropical climate.

*Plant habit*.—Upright mound, typical of Rex *Begonias*.

*Flowering period*.—Blooms throughout the year when grown under warm temperatures, blooms most heavily in spring.

*Height and spread*.—Reaches about 30 cm in height and 38 to 46 cm in spread.

*Cold hardiness*.—U.S.D.A. Zone 10.

*Diseases and pests*.—No disease or pest problems have been observed for the new cultivar.

*Root description*.—Fleshy to fibrous with tubers produced for over-wintering color; a blend of 199A to 199B and 200B.

*Rhizomes*.—Irregularly shaped, an average of 5 cm in length and 1.5 cm in width (larger on older plants), surface is fine bark-like and knobby, color is a blend of 199A, 199B and 200B.

*Root initiation*.—An average of 35 days at soil temperatures of 18° C. from stem cuttings.

*Root development*.—An average of 8 weeks at air temperatures of 20° C. to produce a Rooted stem cutting.

*Growth rate*.—Moderate.

*Propagation*.—Tissue culture is preferred, Stem and leaf cuttings also possible.

Stem description:

*Branching habit*.—Basal leaves and peduncles arise from tubers at surface or from very short stems.

*Stem size*.—An average of 3 cm in diameter and 3.5 cm in length, with the shortest stems an average of 1 cm in length and 7 mm in diameter.

*Stem shape*.—Oval, irregular.

*Stem color*.—A blend of 199A, 199B and 200B.

*Stem surface*.—Thin barked and smooth in texture.

*Stem strength*.—Strong.

*Internode length*.—Average of 5 mm.

Foliage description:

*Leaf type*.—Simple.

*Leaf shape*.—Ovate with base asymmetric (to one side).

*Leaf division*.—Entire.

*Leaf base*.—Cordate.

*Leaf apex*.—Acuminate.

*Leaf venation*.—Main veins are palmate from sinus, color defined under leaf coloration, stiff hairs are present on lower surface that are more abundant on young leaves.

*Leaf margins*.—Crenate, ruffled, with bristly hairs.

*Leaf attachment*.—Petiolate.

*Leaf arrangement*.—Alternate

*Leaf surface*.—Upper surface; rugose, satiny when young and becomes velvety with a sheen to the mottled regions when mature, lower surface; very finely puberulent, young leaves are satiny on upper surface.

*Leaf color*.—Young leaves upper surface; mid region a blend of 138B and 138C, margins and central area a blend of 147A and 202A, veins near center 147A with distal veins a blend of 147A and 202A, young leaves lower surface; mid region 144A, margins, central area and veins N186C, mature leaves upper surface; margins and central area a blend of 147A and 202A, mid region 147A with mottling of 189D (slight tinge of 138B), polka dots develop near margin of 189D (slight tinge of 138B) that coalesce with a mid region mottling, as the leaves age the mottling develops a sheen of N79B, veins 146A, young leaves lower surface; mid region 145B, margins, central area and veins N187B.

*Leaf size*.—Up to 25 cm in length and 14 cm in width when mature.

*Leaf quantity*.—Average of 20 per stem.

*Leaf fragrance*.—None.

*Petioles*.—About 11 cm in length and 5 mm in width on mature leaves, surface is sparsely covered throughout with hairs; about 1.5 mm in length and 158A in color.

*Stipules*.—None observed.

Flower description:

*Inflorescence type*.—Axillary bisexual cyme.

*Number of flowers per cyme*.—4 to 6.

*Peduncles*.—About 10.5 cm in length and 3.8 mm in width (widest at base), color; 146B to 146C and slightly suffused with 183B, surface texture is glabrous with a few sparse hairs near base, flexible and moderately strong.

*Lastingness of flowers*.—A cyme blooms for an average of 3 weeks.

*Flower persistence*.—Self-cleaning.

*Flower type*.—Single.

*Flower fragrance*.—None.

*Flower number*.—Average of 15 flowers per division.

*Flower aspect*.—Nodding and held about 5 cm above the foliage.

*Bracts*.—2, present at base of peduncle, triangular in shape, aristate apex (awn about 4 mm in length), truncate base, about 2.5 cm in length and 1.4 cm width, translucent and suffused in centers with 60C to 60D, waxy texture on upper and lower surface.

Male flowers:

*Pedicels*.—About 2 cm in length and 1.5 mm in width, color; 161B in color and very slightly suffused with 183D, glabrous surface, flexible and moderately strong.

*Flower buds*.—Heart-shaped, about 1.6 cm in length and 1.4 cm in width, a blend of 62B and 62C in color and suffused in very center with 14D, smooth and satiny in texture.

*Flower size*.—About 3.2 cm in diameter and 1.8 cm in depth.

*Tepals*.—4 in number (2 inner and 2 outer), outer tepals: broadly ovate in shape, acute apex, rounded base, average of 3.2 cm in length and 2 cm in width, glabrous and waxy on upper and lower surface, entire margin with very edge slightly recessed on lower surface, color lower surface; a blend of 62B and 62C and suffused in very center with 14D, color upper surface; a blend of 62B and 62C, inner tepals: elliptic in shape, rounded apex, rounded base, average of 1.7 cm in length and 1.4 cm in width, glabrous and waxy on upper and lower surface, entire margin, color upper and lower surface; 62D.

*Corolla form*.—Spreading outward, tepals are un-fused.

*Stamens*.—Numerous (about 180), formed into a globose structure about 7 mm in diameter and height, stamens about 7 mm in length and 1.5 mm in width, filament is very fine, 3 mm in length, and 6D in color, anther is about 2 mm in length, 165D in color and adhered to a petal-like structure that is lanceolate in shape, about 4 mm in width and 2 mm in width and 6B in color, pollen is moderate in quantity and 155B in color.

Female flowers:

*Pedicels*.—About 2.2 cm in length and 1.5 mm in width, color; 161B in color and blended to 146A near base of ovary, glabrous surface, flexible and moderately strong.

*Flower buds*.—Campanulate in shape above a winged ovary, about 2.5 cm in length and 2 cm in width, a blend of 181B, 64B and 64C in color with ovary 181A with area between ovary and wing 146A, smooth and satiny in texture.

*Flower size*.—About 2 cm in depth and 3.5 cm in diameter.

*Tepals*.—5 in number (3 inner and 2 outer), outer tepals; ovate in shape, broadly acute apex, rounded base, average of 1.2 cm in length and width, glabrous and slightly waxy surface, entire margin, color inner surface; a blend of 62A, 62B, and 62C, color outer surface; a blend of 62A, 62B and 183D, inner tepals; broadly elliptic in shape, broadly acute apex, rounded base, average of 1.8 cm in length and 1.3 cm in width, glabrous and slightly waxy surface, entire and slightly wavy margin, color inner and outer surface; a blend of 62B, 62C, and 62D. Corolla form. — Spreading, held slightly upward, tepals are unfused.

*Styles*.—2 in number, cylindrical, stout base and fan-like apex, for basal 1 mm, about 4 mm in length and 4 mm width (at apex), 11B in color.

*Stigmas*.—Crested and curly with short hairs, lobes about 8 mm in length and 4 mm in width, 144BB in color with hairs 11A.

*Ovaries*.—Inferior, about 1.2 cm in length and 1 cm in width with wing 1.2 cm in length and 9 mm in width, color is 181A with area between ovary and wing 146A.

*Mature fruit*.—About 2 cm in length and 1.5 cm in width with wing 2.0 cm in length and 1 cm in width, color 181A, stigma is persistent, hundreds of oblong dust-like seeds (a fraction of a millimeter) pack the lower lobes of the fruit, color 164A.

It is claimed:

1. A new and distinct cultivar of *Begonia* plant named 'Plum Paisley' as herein illustrated and described.

* * * * *